US007761308B2

(12) United States Patent
Falchuk et al.

(10) Patent No.: US 7,761,308 B2
(45) Date of Patent: Jul. 20, 2010

(54) MEDICAL CONSULTATION MANAGEMENT SYSTEM

(75) Inventors: Kenneth H. Falchuk, Newton, MA (US); Jose A. Halperin, Brookline, MA (US)

(73) Assignee: Best Doctors, Inc., Boston, MA (US)

( * ) Notice: Subject to any disclaimer, the term of this patent is extended or adjusted under 35 U.S.C. 154(b) by 1474 days.

(21) Appl. No.: 09/730,299

(22) Filed: Dec. 5, 2000

(65) Prior Publication Data

US 2002/0152096 A1 Oct. 17, 2002

Related U.S. Application Data

(62) Division of application No. 08/818,155, filed on Mar. 14, 1997, now Pat. No. 6,256,613.

(51) Int. Cl.
*G06Q 50/00* (2006.01)
(52) U.S. Cl. .......................... 705/2; 434/322; 434/323; 434/350; 705/3
(58) Field of Classification Search .................. 705/2–4, 705/1, 27, 64, 14, 11, 30, 10, 7; 434/156, 434/236, 262, 322, 350, 118, 219, 323, 362, 434/365, 356; 379/76; 273/430; 707/5, 707/1, 3, 7, 10, 102; 709/201, 217, 226, 709/228; 235/382
See application file for complete search history.

(56) References Cited

U.S. PATENT DOCUMENTS

| 4,539,435 | A | * | 9/1985 | Eckmann | 379/76 |
|---|---|---|---|---|---|
| 5,002,491 | A | * | 3/1991 | Abrahamson et al. | 434/322 |
| 5,517,405 | A | * | 5/1996 | McAndrew et al. | 706/45 |
| 5,727,950 | A | * | 3/1998 | Cook et al. | 434/350 |
| 5,810,605 | A | * | 9/1998 | Siefert | 434/362 |
| 5,853,292 | A | * | 12/1998 | Eggert et al. | 434/262 |
| 6,125,350 | A | * | 9/2000 | Dirbas | 705/2 |
| 6,283,761 | B1 | * | 9/2001 | Joao | 434/236 |
| 6,546,230 | B1 | * | 4/2003 | Allison | 434/350 |

OTHER PUBLICATIONS

Minnesota Medical Association Report on Telemedicine article, Sep. 1996, URL: <http://www.mnmed.org/Protected/telemedicine.pdf>.*

(Continued)

*Primary Examiner*—Gerald J. O'Connor
*Assistant Examiner*—Natalie A Pass
(74) *Attorney, Agent, or Firm*—Patent GC LLC

(57) ABSTRACT

A medical consultation support system which transfers a structured request for consultation from a primary care physician's client computer to a supervisory host computer. The structured request together with any additional information related to the request, form a machine-readable collection of information. At the supervisory computer, the request is reviewed by a receiving staff physician who designates a specialist and retrieves supporting documentation related to the consultation request from databases of medical information. The supervisory computer then transmits the request for consultation and at least an identification of the selected supporting documentation to the selected specialist for review, and thereafter receives a comment from the selected specialist. The supervisory computer further stores the request for consultation and the comment as a structured case history item in the database of medical information. A consultation may further be a source of continuing legal education credits for the requesting physician.

4 Claims, 3 Drawing Sheets

OTHER PUBLICATIONS

Richert, C. Increasing Your Consultation Base via WWW. Nov. 1996, Div. Pathology Informatics, Univ of Pittsburgh Med.Ctr website. [Retr.Dec. 29, 2004].Retr.Internet.<http://web.archive.org/web/19970128170752/http://www.pathology.pitt.edu/apiii/author/work2c.htm>.*

1995 Innovative Use of Technology Award Winners. NASCIO website. 1995. [Retrieved on Oct. 12, 2005]. Retrieved from Internet. URL: <http://www.nascio.org/awards/1995awards/aw95it.cfm>.*

Orthopaedists investing in home study. AAOS Bulletin. vol. 43, No. 3, Jul. 1995. <Retrieved on Oct. 12, 2005>. Retrieved from Internet. URL: <http://www.aaos.org/wordhtml/bulletin/homestdy.htm>.*

Bringing Health Care Online: The Role of Information Technologies, Chapter 5: Telemedicine: Remote Access to Health Services and Information article, U.S. Govt.: OTA-ITC-624. Sep. 1995, URLs: <http://www.wws.princeton.edu/ota/disk1/1995/9507/950707.PDF> and <http://www.wws.princeton.edu/ota/disk1/1995/9507/950701.PDF>.*

Galewitz, P. Doctors Can Now Get Continuing Education On-Line, Palm Beach Post. West Palm Beach, Fla.: Jul. 8, 1996, p. 13.*

Tangalos, E. Enabling Technologies for Telepresence, Mayo Clinic/Mayo Foundation, 1996 IEEE, Proceedings of National Forum '95.*

Fontelo, P.A. Continuing medical education on the World Wide Web. Military Telemedicine On-Line Today, 1995.'Research, Practice, and Opportunities', Proceedings of the National Forum Mar. 27-29, 1995.[Retrieved on Nov. 5, 2007]. Retr. Internet.URL:<http://ieeexplore.ieee.org/iel3/3745/10944/00504546.pdf?tp=&arnumber=504546&isnumber=10944>.*

Galewitz, P., Doctors Can Now Get Continuing Education On-Line. Palm Beach Post. Jul. 8, 1996. [Retrieved on Nov. 5, 2007]. Retrieved from Internet. URL: <http://proquest.umi.com/pqdweb?did=66323909&sid=4&Fmt=3&clientId=19649&RQT=309&VName=PQD>.*

University of Alabama Pediatric Surgery Web Site. Nov. 1996. [Retrieved on Nov. 5, 2007]. Retrieved from Internet. URL: <http://web.archive.org/web/19961125115120/http://pedsurg.surgery.uab.edu>.*

CME Gateway. Dec. 1996. [Retrieved on Nov. 5, 2007]. Retrieved from Internet. URL: <http://web.archive.org/web/19961222183248/http://www.cmegateway.com >.*

Anonymous. Continuing medical education on the Web. Patient Care. Oradell: Feb. 15, 1997. vol. 31, Iss. 3; p. 43. [Retrieved on Nov. 5, 2007]. <URL: http://proquest.umi.com/pqdweb?did=11088353&sid=3&Fmt=2&clientId=19649&RQT=309&VName=PQD>.*

McEnery, K.W., Computers in Radiologic Education: The Internet, World-Wide Web, and Mosaic: an Overview. American Journal of Roentgenology. 1995. vol. 164, 469-473. [Retrieved on Nov. 5, 2007]. Retrieved from Internet. URL: <http://www.ajronline.org/cgi/reprint/164/2/469.pdf>.*

* cited by examiner

MEDICAL CONSULTATION MANAGEMENT SYSTEM

CROSS REFERENCES TO RELATED APPLICATIONS

The present patent application is a divisional of U.S. Ser. No. 08/818,155, Falchuk, et al., A medical consultation management system, filed Mar. 14, 1997 now U.S. Pat. No. 6,256, 613.

FIELD OF THE INVENTION

This invention relates to health care management systems and more particularly to a system for facilitating and managing consultation between primary care physicians and specialists.

BACKGROUND OF THE INVENTION

A need exists for new approaches to medical consultation, physician referral and continuing medical education. In the United States, health care costs have increased since 1960 at the average annual rate of 11.3%, over three times the rate of inflation, resulting in intense scrutiny of both the costs and quality of health care from private, public and governmental institutions.

One solution has been managed care, a concept that has slowed the rate of growth and, in some instances, actually cut costs through the formation of closed panels of providers who deliver care at a pre-negotiated price utilizing managed and controlled approaches. Under managed care, primary care physicians treat the majority of the patients and serve as gatekeepers to triage to specialists.

As medical and technological knowledge increases, primary care physicians must keep abreast of rapidly changing developments. Unfortunately, much of this new knowledge resides with expensive specialists. Consumers are concerned that their primary care physician is limited in his or her access to such information because of the expense of using the specialist, and the physician gatekeeper is viewed frequently by the public as the one who avoids incurring expenses to the system rather than helping the patient.

Primary care physicians frequently need access to leading specialists in a matter of hours when difficult problems arise. Although consultations with specialists in the HMO's provider network suffice in most instances, the necessary expertise may not always be available "in panel," thus requiring timely access to an expert outside of the panel.

There is consequently a need for managed, direct access to outside medical consultants. Such access helps avoid inaccurate, incomplete, or uncertain diagnoses which can result in inappropriate or excessive care, as well as the liability and operating costs which result when physicians do not receive the necessary help at an early stage in treatment.

HMOs also have an increasing need to better document the performance of each doctor in order to better understand and influence physician behaviors, to modify treatments to coincide with established patient outcomes, to better disseminate improve methods as they arise. Physicians desire ways of obtaining necessary or useful knowledge in an educational format consistent with how they have been trained during their professional life. By better documentation of the knowledge gained through experience, HMOs can improve patient outcomes and decrease the risk of costly malpractice claims. There is accordingly a need for better procedures for encouraging and documenting the continuing medical education which is gained when primary care physicians consult with specialists having particular expertise.

The varying skill levels and the variety of training and backgrounds of providers further complicates the delivery of quality, lowest, cost care. As provider groups enlarge and become less homogeneous, the physician population in organizations is growing both in size and in diversity of knowledge and experience. As a result, educating physicians and other medical staff so as to ensure standards and "best practice" protocols has become a critical factor to effective delivery of health care services. Moreover, health care administrators also want these "best practice" standards to be followed in order to eliminate unnecessary medical procedures without increasing legal liability or stifling a physician's flexibility to practice medicine. There is accordingly a need to integrate the communication of proven practices and protocols which should be applied to special situations with the process of seeking consultation on those special situations.

SUMMARY OF THE INVENTION

In a principal aspect, the present invention takes the form of a medical consultation support system in which a client computer, such as a personal computer or a terminal of an existing medical support system, is provided with means for accepting a structured request for consultation from a primary care physician. The client computer also preferably includes means for including additional information related to the request, such as existing data files containing patient history information, medical image data, laboratory results, pathologies, etc., forming a transmittable, machine-readable collection of information relating to the consultation request.

In accordance with the invention, this structured consultation request is received and processed by a supervisory host computer which includes means for visually displaying at least a portion of the request for consultation for preliminary review by a receiving staff physician. The supervisory computer accepts the designation of a specialist from the staff physician, and additionally provides means for retrieving and assembling selected tutorial and background information, including related published articles, tutorial background lessons, practice and protocol documentation, and records of prior consultations which are related to the current consultation request, all of which are stored in one or more databases of medical information accessible to the supervisory host computer. The supervisory computer then transmits the request for consultation, together with at least the identification of the assembled supporting documentation, to the selected specialist for review.

The supervisory computer thereafter receives the responsive comment from the selected specialist, and transmits this response, along with the selected tutorial and/or background information, to the requesting primary care physician. The supervisory computer further stores the request for consultation, including the specialist's responsive comment and an identification of the cited supporting material, as a structured case history item in the database of medical information where it may be accessed for future reference.

Each consultation is further stored as a recorded learning event associated with the requesting primary care physician, and used to generate a report of continuing legal education credits earned by the requesting physician while participating in the managed consultation sessions.

The invention may be advantageously implemented by forming both the request for consultation and the specialist's responsive comments into one or more hypertext documents linked to the supporting materials, forming highly accessible case history documentation which may be readily manipulated using standard hypertext processing facilities.

These and other features of the invention may be more clearly understood by considering the following detailed description of a preferred embodiment of the invention. During the course of this description, frequent reference will be made to the attached drawings.

DESCRIPTION OF THE PREFERRED EMBODIMENT

Figure 1:
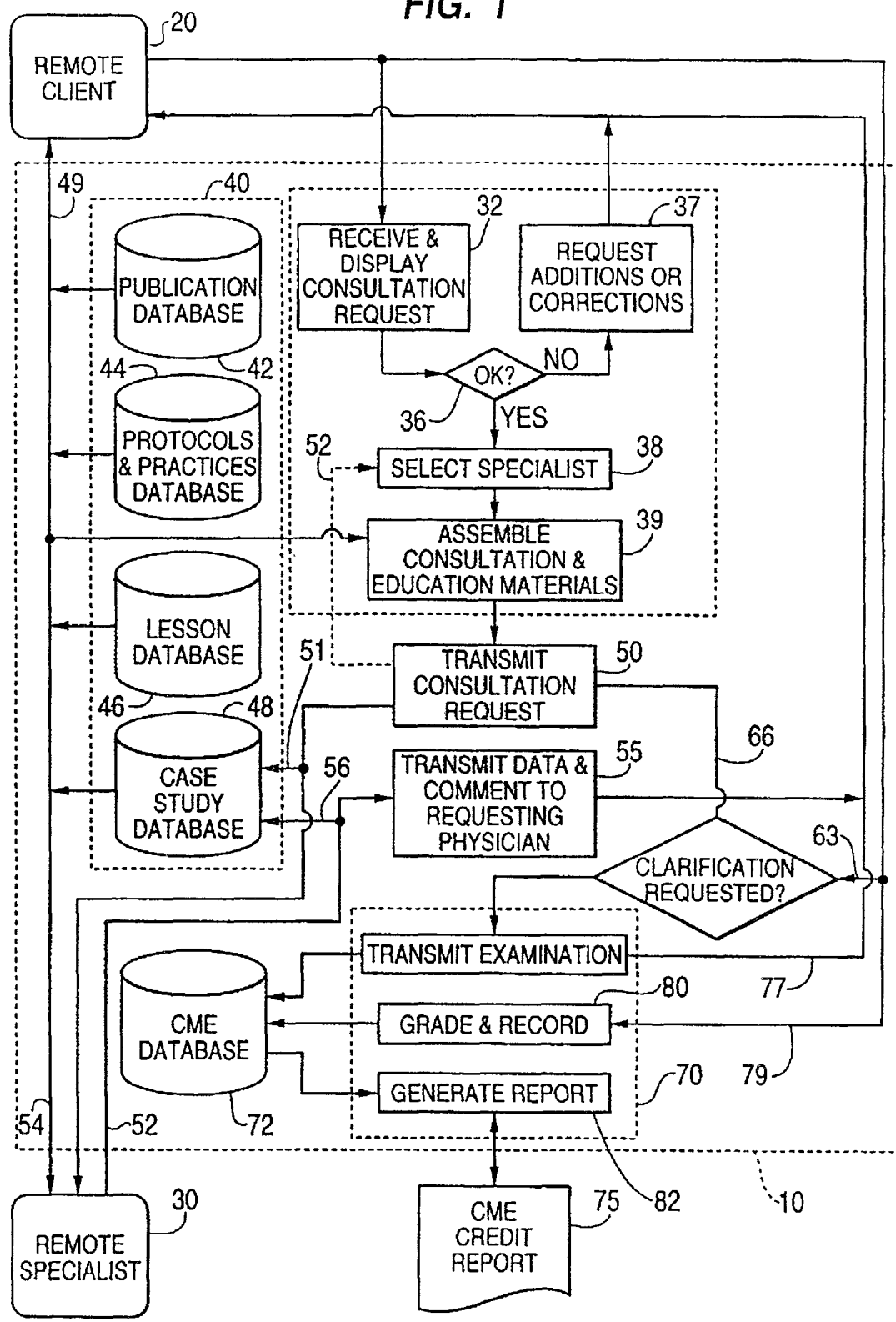
FIG. 1 is a data flow diagram depicting the principle functions performed by the supervisory host computer during processing and management of a consultation session between a primary care physician and a selected specialist.

A supervisory host computer 10 used in the preferred embodiment of the invention operates as illustrated in FIG. 1 to perform three principal concurrent functions: (1) it manages and records a consultation session between a primary care physician and a selected specialist, both of whom are typically geographically remote from the host computer; (2) it both uses and augments a database of medical information which includes a collection of case study items, each containing information which was utilized during the course of a given consultation session; and (3) it builds and uses a database of "learning events" associated with each participating primary care physician, thereby creating reports for participating physicians which certify their participation in consultation sessions entitling them to continuing medical education credits.

Figure 2:
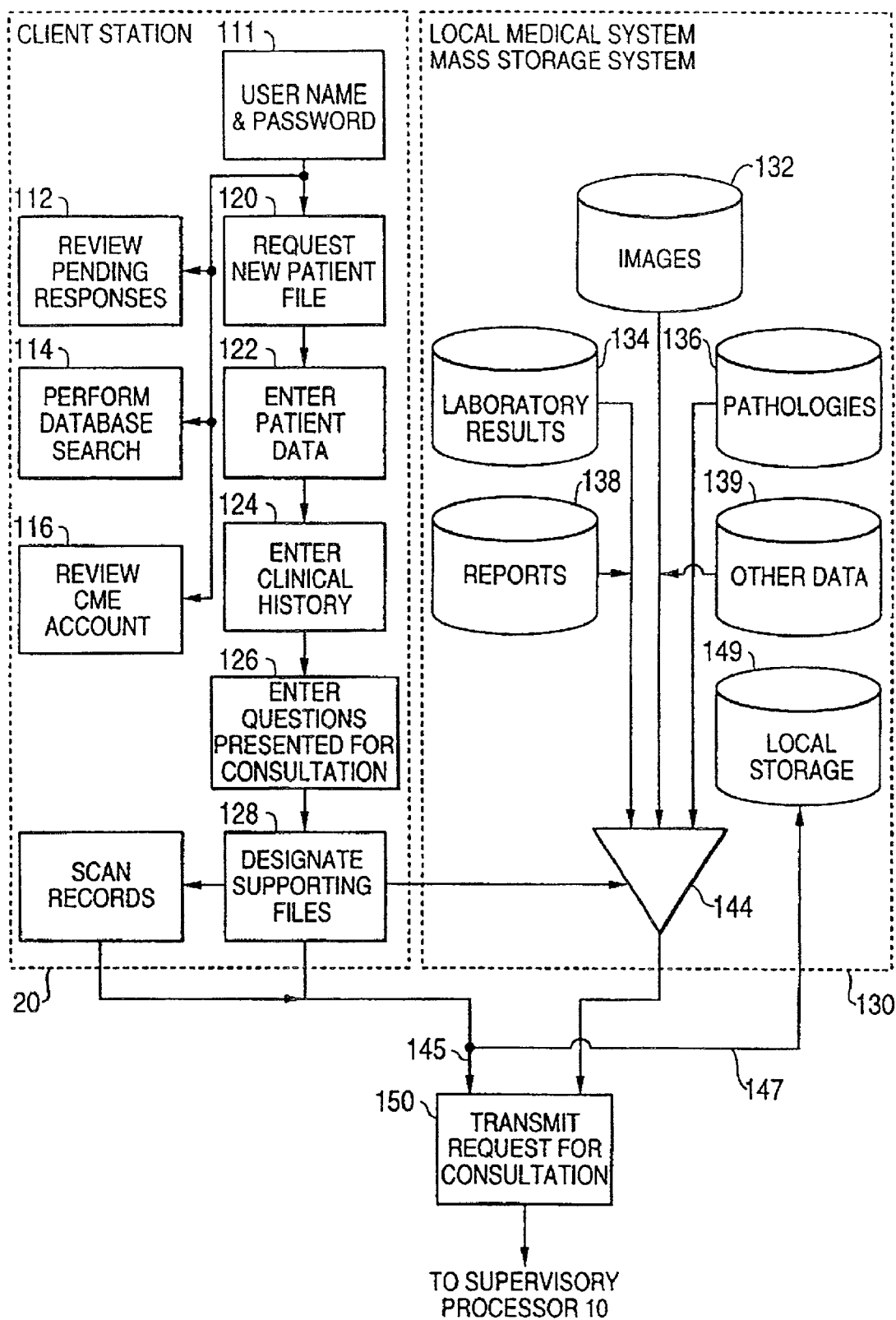
FIG. 2 is a data flow diagram illustrating the operation of the client computer during the formulation and transmission of a request for consultation.

As seen in FIG. 1, and detailed in FIG. 2, the primary care physician utilizes a client computer station 20 to formulate and transmit a request for consultation to the supervisory host computer indicated generally at 10, which processes and relays the request to a remote specialist computer 30. The supervisory host computer 10 is typically located remotely from the client computer 20 and serves a large number of client computers in a client/server relationship. The host computer 10 receives the request for consultation and displays information contained in the request for initial review by a staff physician as indicated at 32. Programmatic tests are performed by the client computer 20 and/or the supervisory computer 10 to test the validity of data entered into the formatted fields of the consultation request. Consequently, the staff physician need only review the request to insure that its content is adequate to enable the selection of one or more specialists having expertise in the specialty in which consultation is sought. If the content is deficient, the staff physician notes the deficiency in a rejection message returned to the requesting physician as indicated at 36 and 37 in FIG. 1.

The staff physician then selects a specialist to handle the request as indicated at 38 and forwards the request to the selected specialist together with selected materials which are obtained and assembled at 39 from an information database 40 which stores medical information which may be relevant to the request.

This information database 40 advantageously includes a publication database 42 consisting of abstracts or the full text of articles in medical journals, either stored locally in the host processor's mass storage facility, or in an available medical database, such as Medline/Medlars, connected to the host supervisory processor 10 over a data communications network (not shown). In addition, the information database 40 further advantageously contains a tutorial database 44 containing background lessons which will be made selectively available to the requesting physician as an adjunct to, and in support of, the comments to be received from the specialist. The information database 40 further advantageously contains a database 46 of approved protocols and practices which, to the extent applicable to the requested consultation, should be called to the attention of the requesting physician. Finally, the database 40 advantageously includes a case history database 48 which is augmented by case study data produced by the administered consultation sessions themselves, as hereinafter described.

Standard information retrieval techniques may be employed to facilitate the retrieval of relevant information from the information database 40. The text of the "question" posed by the requesting physician and contained in the consultation request received at 32 may be used as a free-form retrieval request to find items of probable interest using conventional text content matching algorithms. In addition, the staff physician may supplement the retrieved collection using category-specific search requests, and may narrow the collection by eliminating items of little use which were identified by the automated search techniques. Materials which may provide tutorial assistance to the requesting physician but which need not be submitted in complete form to the selected specialist are nevertheless advantageously listed in the consultation request transmitted to the specialist so that the specialist is made aware of the support materials which are to be made available to the requesting physician. As indicated at 49, direct search requests may also be directed to the information database 40 by the primary care physician, using the remote client computer 20 in support of, or independently of, a request for consultation.

As seen in FIG. 1, the supervisory computer 10 is coupled by conventional communications facilities to a remote specialist computer 30 to which the consultation request is forwarded as indicated at 50. The transmission preferably takes the form of a notification message directed to the mailbox of the specialist who was selected by the staff physician as indicated at 38. The actual content of the consultation request, together with an identification of the support materials to be made available to the requesting physician, may, accordingly, be included with the notification message, or later transmitted later upon request by the specialist.

All information supplied to the specialist, including both the original request for consultation and the identification of (database pointers to) the database information assembled at 39 in support of the request, is stored in a case history file established within the case study database 48 for this consultation, as indicted at 51. Further information is thereafter added to this case history file as the consultation proceeds. As discussed in more detail below in conjunction with FIG. 3, the supervisory computer 10 advantageously stores the request for consultation in the case history file in the form of a summary document expressed in hypertext markup language (HTML) which incorporates links other HTML documents and/or supporting materials from the information database 40. The consultation request may then be reviewed by the selected specialist using a hypertext document browser which retrieves and displays selected linked HTML documents and linked files as needed directly from the information database 40.

To insure that the request for consultation is handled in a timely fashion by the selected specialist, the staff physician or other supervisory personnel is notified, as indicated at 52, in the event that an acknowledgment is not received from the remote specialist computer 60 within a predetermined duration. In the absence of an indication that the request for consultation has been received and is being handled, delay notification 52 permits the staff physician to select a different available specialist to handle the request in timely fashion when necessary.

Using the facilities provided by the remote specialist computer 30, the selected specialist enters a text comment answering the consultation request to form information structured comment information, which may include reference to supporting articles, lessons, protocols or prior case studies in the information database 40. As indicated at 54, the specialist may make independent search requests to the database 40 to obtain information in aid of the consultation, so that the citations supplied by the consulting specialist may include not only those materials identified by the automated searches performed by the staff physician but also supplemental materials newly cited by the specialist. Moreover, the specialist may append any other data which is available to the structured comment information, including image data or materials available to the specialist from another database (not shown).

The structured comment information from the consulting specialist is then returned to the supervisory host computer 10 which forwards the comment information to the remote client computer as indicated at 55. In addition, the supervisory computer 10 also stores the responsive comment in the case study database 48 for inclusion the case history file established at 51 to hold the original consultation request, as indicated at 56.

The requesting primary care physician is according supplied with the advisory comments of the consulting specialist and a body of documented supporting materials, which may include relevant published articles from database 42, documented practices and protocols from database 44, tutorial lessons material from the database 46, and prior relevant case histories from the case study database 48. As discussed later in conjunction with FIG. 3, the response to the consultation request which is supplied to the physician also advantageously takes the form of a summary document expressed in hypertext markup language (HTML) and includes links to supporting HTML documents and retrieval supporting documents supplied by the specialist. Using an HTML browser, the requesting primary care physician can, accordingly, review the specialist's comments and the supporting documentation using the HTML browsing facilities of the client computer 20.

Although the initial comment and documentation supplied by the consultant may in many cases wholly satisfy the needs of the requesting primary care physician, clarification may be requested when needed. The clarification request message is transmitted to the supervisory computer 10 from the remote client 20 and received as indicated at 63. The incoming message is examined at 65 to determine whether a clarification or requested or, in the alternative, that the requesting physician wishes to conclude the consultation. If the received message is a request for clarification, it is transmitted to the specialist for further comment as indicated at 66; otherwise, a CME accreditation module indicated generally at 70 is notified that the consultation has been successfully concluded.

The accreditation module 70 administers a database 72 which records information concerning the consultation sessions and produces accreditation reports 75 which may be submitted to the responsible accreditation authority to certify that the requesting physician is entitled to continuing medical education (CME) credits based on his or her participation in the consultation session. When required for credit, the requesting physician may also be requested to complete an examination form testing the knowledge gained, in which case an examination is made available the requesting physician as indicated at 77. This examination form may also be advantageously implemented by an HTML form which is transmitted to the requesting physician, completed, and resubmitted to the supervisory computer 10 as indicated at 79. The completed examination form is then graded and the results posted to the CME database 72 as indicated at 80. The credits accumulated by individual primary care physicians who have participated in learning sessions are then detailed in the CME credit report 75 which is thereafter produced for submission to the responsible accrediting body as indicted at 82.

FIG. 2 of the drawings illustrates the principal functions performed by the remote client computer, seen at 20 in FIG. 1, during the initial formation of a request for consultation. Each request for consultation identifies the particular primary care physician to whom the specialist's comments and supporting materials will be returned and to whom CME credit will be given for participation in the consultation learning event. The requesting physician accordingly supplies his or her user name and an assigned password at 111 to gain access to system services.

After successful entry, the authorized user is informed of any pending responses from the supervisory host computer 10 as indicated at 112, including requests for additions or corrections to prior consultation requests, specialist's comments and supporting materials responsive to prior requests, clarifying comments from specialists in response to prior clarification requests, and pending examinations to be completed to fulfill CME requirements. As previously noted, and as indicated at 114 in FIG. 2, the system also allows the physicians to make direct search requests for information from the systems information database 40, permitting the physician to readily review published articles, practices or protocols, available tutorial lessons, or the content of any prior consultation case history, including those in which he or she participated. In addition, as indicted at 116, the primary care physician may request the display of his or her participation in prior consultations to obtain information on earned CME credits.

When the primary care physician or other authorized user requests a consultation, as indicated at 120 in FIG. 2, a sequence of screen displayed forms is presented for completion, guiding the entry of data describing the patient at 122, the patient's clinical history at 124, and the particular question being posed by the primary care physician for comment by the specialist at 126. These forms may be defined and produced by a special-purpose program executing locally on the remote client computer or may be defined by HTML documents with imbedded <FORM> and <INPUT> tags which define the fields to be completed and which are displayed for entry by a general purpose HTML viewer/browser program executing on the client computer. The resulting structured output records or completed HTML form(s) constituting the request for consultation are then submitted to the supervisory host computer 10 for processing.

In addition to the data entered on the request definition forms presented to the user at 122-126 as seen in FIG. 2, medical records may be selected from existing files in the local medical record database indicated generally at 130 in FIG. 2. These supporting files, which may be appended to the request for consultation, may include medical image data (x-ray, NMR, ultrasound, etc.) as indicated at 132, laboratory test result data at 134, pathologies at 136, patient records and reports at 138, and other data at 139. When available data does not exist in machine readable form in existing data files, it may be converted into scanned image data which may be appended to the request for information as indicated at 142. Image annotation utilities may be used to allow the requesting physician to add overlay graphical annotations, pointers and the like onto image data transmitted with the request in order to facilitate review by the specialist or reviewers who later inspect the case history file which records the consultation.

As depicted at 144, the records from the local database 130 which are to be appended to the request are transmitted to the supervisory host processor 10 for inclusion in the case history file. The data entered to define the consultation request at 122 - 126, together with the newly scanned data, is both transmitted to the supervisory processor 10 as indicated at 145 and transferred to the local mass storage system 130, along with pointers to the existing records which are merged at 147 for transmission to the supervisory computer 10 at 150, but which do not need to be stored again since those records already exist in the local mass storage system 130. In this way, a complete local record of all requests for consultation is maintained within the local storage file 149, as well as in the case history database 48 maintained by the supervisory processor 10.

Both the request for consultation and the specialist's comments are advantageously submitted to the supervisory computer 10 as HTML forms. The supervisory processor 10 may then convert the completed forms into closely similar HTML documents for inclusion in the case history file and transmittal to the specialist, so that the forms as displayed on screen and retained in the case history file closely resemble the forms originally completed at the time of data entry. The conversion of completed HTML forms into conventional HTML documents can be performed by the supervisory processor's execution of a Common Gateway Interface (CGI) script program which validates the entries, issues a request for additions or corrections as seen at 37 in FIG. 1 if the entries are incomplete or invalid, and otherwise creates new case history HTML documents for use during the consultation.

Figure 3:
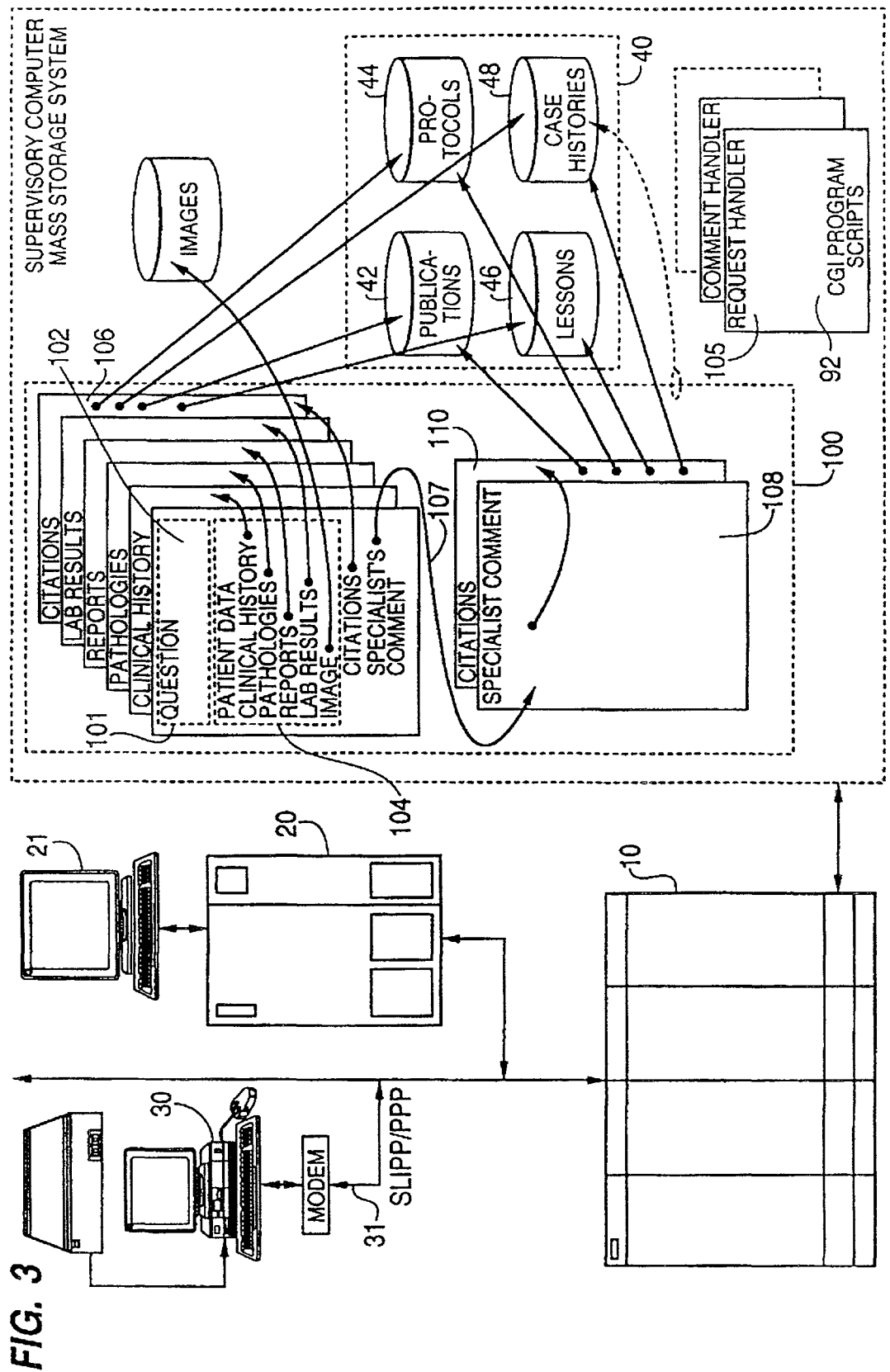
FIG. 3 is a data flow diagram illustrating the manner in which hypertext markup language (HTML) documents may be advantageously employed to implement the communications which occur during the consultation as well as to form a readily reviewable case history file for later use.

The invention may be advantageously implemented using a conventional HTML processing and data communication infrastructure. As illustrated in FIG. 3, the supervisory host processor 10 may be interconnected with the remote processor 20 via a standard data link using the Telecommunications Control Protocol/Internet Protocol (TCP/IP). The selection of this common protocol yields a system that is essentially device independent, so that a wide variety of workstations, personal computers and mainframes may be employed to implement the nodes of the system. As an example, the client computer 20 may be implemented as by a workstation 21 on an local, minicomputer based system which includes its own shared mass storage system of the type indicated at 130 in FIG. 2, whereas the remote specialist computer 30 may be a personal computer connected to the host 10 via a modem and a dial-up SLIPP/PPP connection 31. Moreover, by using the HTML document format for request and comment forms, subscribers may access and use the system using special purpose or conventional HTML browser/viewer software (e.g., a Mosaic or Netscape browser), and the supervisory computer 10 may process these HTML forms using CGI script programs 92 to produce HTML documentation which may be conveniently accessed, reviewed and browsed by the participants to the consulting session. CGI script programs also create the HTML case histories (HTML request forms, comment forms and linked HTML and FTP support files) in the database 48, which can also be, searched, reviewed and browsed by subscribers.

As illustrated at 100 in FIG. 3, an individual case history thus advantageously includes a table of contents HTML page 101 which includes, or links to, the question posed for consultation 102 and patient information at 104 (with further links, if necessary, to other HTML pages containing pathologies, reports, lab results, and image data), and a citation listing 106 with links to cited supporting material in the supervisory computer's mass storage system, such as publications, protocols, lessons and other case histories. When the specialists comment(s) are received for processing, the comment handler CGI script seen at 105 adds a link to the request HTML page at 107 which identifies the comment HTML page 108, and the comment page 108 in turn, contains its own citation list 110 containing links to whatever additional supporting materials in the database 40 have been cited by the specialist.

The links themselves may advantageously take the form of conventional Uniform Resource Locators (URLs), permitting citations to be made to information sources outside the system which are available via the World Wide Web (WWW), FTP or Telnet. As will be understood, the supervisory computer itself can also advantageously operate as a World Wide Web server which is hence accessible to authorized users from any computer equipped with an Internet connection and standard web browsing client software, allowing primary care physicians to have access to consulting services from remote locations in emergency situations.

It should be understood that the embodiment of the invention which has been described is merely illustrative of one application of the principles of the invention. Numerous modifications may be made by those skilled in the art without departing from the true spirit of the invention.

What is claimed is:

1. A method of providing continuing medical education credit to a first physician for a consultation between the first physician and a second physician, the first and second physicians being coupled via a telecommunications system to an intermediary having a processor and a storage device to which the processor has access, the method comprising the steps of receiving a request for a consultation from the first physician via the telecommunications system at the processor of the intermediary, the processor of the intermediary being programmed to manage and record the consultation between the first physician and the second physician, the processor of the intermediary storing the request in the storage device;

receiving by the processor of the intermediary a selection of the second physician made by a staff physician in the intermediary, the second physician having an expertise in a specialty in which the consultation is requested by the first physician;

sending by the processor of the intermediary the stored request to the selected second physician via the telecommunications system;

receiving by the processor of the intermediary a comment made with regard to the consultation via the telecommunications system from the selected second physician and the processor of the intermediary storing the comment;

providing by the processor of the intermediary the stored comment from the selected second physician to the first physician via the telecommunications system;

on conclusion of the consultation, an accreditation module of the processor of the intermediary recording information concerning the consultation in a continuing medical education database accessible to the processor, the information being associated with the first physician; and creating, by the accreditation module, an accreditation report for the first physician from the information in the continuing medical education database, the accreditation report comprising a certification of the continuing medical education credit earned by the first physician from participation in the consultation.

2. The method of providing continuing medical education credit set forth in claim 1 wherein the method further comprises the steps of:

retrieving by the processor of the intermediary instructional material relevant to the comment and the consultation selected by the staff physician from an information data base to which the processor has access; and providing the instructional material to the first physician via the telecommunications system.

3. The method of providing continuing medical education credit set forth in claim 1 wherein the method further comprises the steps of:

providing by the accreditation module via the telecommunications system an examination based on at least the comment to the first physician;

receiving at the accreditation module answers for the examination from the first physician; and grading by the accreditation module the received answers, the first physician being entitled to the medical education credit if the first physician passes the examination.

4. The method of providing continuing medical education credit set forth in claim 2 wherein the method further comprises the steps of:

providing by the accreditation module an examination based on at least the instructional material to the first physician via the telecommunications system;

receiving at the accreditation module answers for the examination from the first physician via the telecommunications system; and grading by the accreditation module the received answers, the first physician being entitled to the medical education credit if the first physician passes the examination.

\* \* \* \* \*